United States Patent [19]

Gerrard

[11] Patent Number: 4,799,786

[45] Date of Patent: Jan. 24, 1989

[54] METHOD OF DIAMOND IDENTIFICATION

[75] Inventor: Donald L. Gerrard, West Ewell, England

[73] Assignee: The British Petroleum Company p.l.c., London, England

[21] Appl. No.: 9,364

[22] PCT Filed: Jun. 12, 1986

[86] PCT No.: PCT/GB86/00340

§ 371 Date: Feb. 3, 1987

§ 102(e) Date: Feb. 3, 1987

[87] PCT Pub. No.: WO86/07457

PCT Pub. Date: Dec. 18, 1986

[30] Foreign Application Priority Data

Jun. 13, 1985 [GB] United Kingdom ............... 8514992

[51] Int. Cl.$^4$ .................. G01J 3/44; G01N 21/87
[52] U.S. Cl. ......................... 356/30; 356/301
[58] Field of Search ........................... 356/30, 301

[56] References Cited

U.S. PATENT DOCUMENTS 4,397,556  8/1983  Müller ............................... 356/301
4,693,377  9/1987  Gerrard et al. ....................... 356/30

FOREIGN PATENT DOCUMENTS 2140555  11/1984  United Kingdom ............... 356/301

OTHER PUBLICATIONS

Melles Griot, *Optics Guide 3*, 1985, pp. 1, 333, 350, 351.
Solin et al., *Physical Review B*, vol. 1, No. 4, Feb. 15, 1970, pp. 1687–1698.

*Primary Examiner*—F. L. Evans
*Attorney, Agent, or Firm*—Morgan & Finnegan

[57] ABSTRACT

A method for the identification of diamonds in which a sample (3) to be identified is placed in a beam of monochromatic laser radiation (2) of pre-determined wavelength. The scattered Raman radiation emitted from the sample (3) is passed through a filter (4) adapted to pass only scattered Raman radiation of frequency characteristic of a diamond. The filtered radiation is then detected by the human eye (5) or a photocell device.

4 Claims, 1 Drawing Sheet

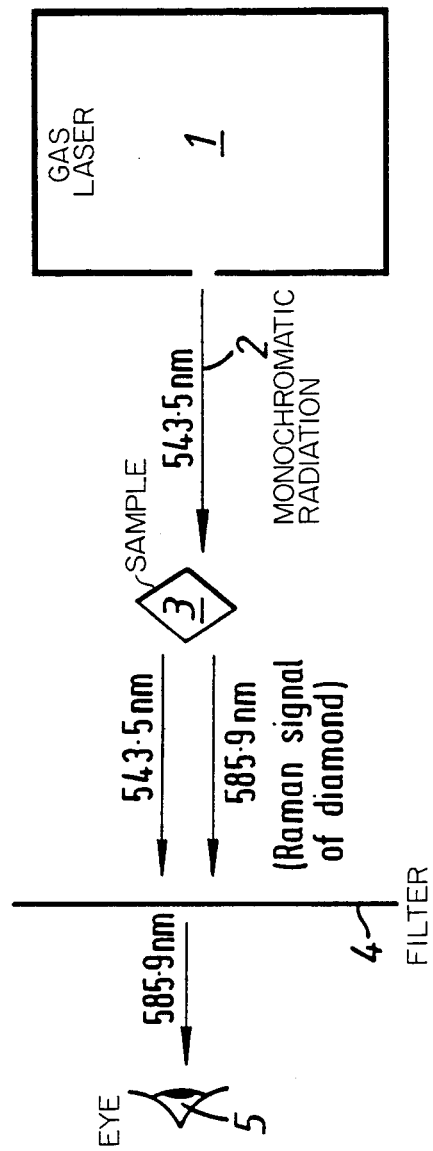

METHOD OF DIAMOND IDENTIFICATION

The present invention relates to an identification technique and more particularly relates to the identification of diamonds as opposed to artificial diamonds, zircon or similar materials.

It is often useful for example in the jewelry trade to unambiguously differentiate between cut diamonds (gem grade) and artificial diamonds such as those made from zircons. In Raman spectroscopy a monochromatic beam of light is directed onto a sample and observations are made on the scattered radiation. Monochromatic light sources of different frequencies can be used such as gas lasers. The Raman signal from a diamond has been found to be highly specific and the present invention relates to a device for identifying diamonds by use of this property.

Thus according to the present invention, there is provided a method for the identification of diamonds comprising the steps of (a) placing a sample to be identified in a beam of monochromatic laser radiation of predetermined wavelength, (b) passing the scattered Raman radiation from the sample through a filtering means adapted to pass only scattered Raman radiation of frequency characteristic of a diamond, and (c) detecting the filtered radiation.

Preferably the source of radiation is a gas laser producing monochromatic radiation in the green parts of the spectrum. The means for detecting the excited Raman radiation is preferably the human eye or a detector based on a photocell but other suitable forms of detection may also be used. The filtering means is preferably located at right angles to the scattered beam of radiation. The filtering means may comprise a thin glass slide having a suitable coating. Filters are available from manufacturers (such as Melles Griot) and are characterized in terms of the wavelength of the incident radiation.

The invention also includes a device for the identification of diamonds comprising a source of laser radiation adapted to provide a monochromatic beam, means for supporting a sample to be identified in the path of the monochromatic beam, a filtering means adapted to pass only scattered Raman radiation of frequency characteristic of a diamond and means for detecting the scattered Raman radiation passed by the filtering means.

Conventional analysis of materials by Raman spectroscopic techniques involves the use of expensive optical equipment such as a monochromator together with a detector such as a photomultiplier tube or a diode array (see our copending UK patent application No. GB 2140555 A).

However it has been found that in the case of a diamond the Raman signal resulting from its irradiation with a monochromatic beam is relatively intense. By use of a narrow band pass filter a means of identification of diamonds from those of the artificial variety has been produced.

By the use of a gas laser giving an output in the green region of the visible spectrum, the Raman shift caused by a diamond is sufficiently towards the red region to allow ready identification using conventional laser safety goggles, the goggles filtering the unshifted laser radiation. A helium/neon laser which normally gives an output in the red region of the spectrum, near 632.8 nm can be modified to give an output near 543.5 nm. Such a laser is much less expensive than other green lasers and is suitable for observation of the Raman signal eye after removal of unshifted laser radiation by a suitable filter. The preferred range of wavelengths for the incident monochromatic laser radiation is from 450 to 650 nanometers.

The invention will now be described by way of example only and with reference to the accompanying drawing.

A low powered gas laser 1 of the helium/neon type (supplied by Melles-Griot (Netherlands)) was adapted to give an output near 543.5 nm and to direct a beam of monochromatic radiation 2 onto a sample 3 in a holder (not shown). A filter 4 adapted to pass radiation having a wavelength near 585.9 nm (the Raman signal of diamond) was positioned at right angles to the axis of the sample holder and the laser 1. A detector 5, in this case the human eye, was positioned behind the filter 4.

During use, a sample of either a diamond or an artificial diamond was located in the sample holder. A beam of monochromatic laser radiation of wavelength 543.5 nm was directed onto the sample. Scattered radiation which has not undergone a Raman transition characteristic of a diamond was removed by the filter. If the sample was a real diamond, the Raman signal of wavelength 585.9 nm was passed by the filter and was detected. Thus depending on whether or not a diamond is present in the sample holder the observer will detect a signal. This enables a differentiation or identification of diamond and artificial diamonds to be obtained.

It is also envisaged that the device could be portable in nature. Thus an operator, holding a portable source of laser radiation, could direct the radiation onto a sample. By viewing the scattered radiation through a suitable filter, the absence or presence of diamond may be rapidly ascertained. A device which uses the human eye as a detector will clearly have advantages of cheapness and reliability as opposed to devices dependent upon electronic or other forms of detector.

I claim:

1. A method for distinguishing between diamonds comprising the steps of:
   (a) irradiating a gem to be distinguished with a beam of monochromatic laser radiation, the laser radiation being produced by a low powdered laser and having a wavelength in the range about 450 to 550 nanometers;
   (b) passing any resultant scattered Raman radiation from said gem through an optical filter adapted to pass only scattered Raman radiation of wavelength characteristic of diamond and,
   (c) detecting said filtered radiation by the eye of an observer thereby to enable identification of said gem as a diamond or otherwise.

2. A method according to claim 1 in which said laser radiation is produced by a helium/neon laser and has a wavelength at or near 543.5 nanometers.

3. A method according to claim 1 or 2 in which the optical filter comprises a portion of glass having a filtering coating.

4. A method according to claim 1 or 2 in which the filtering means is at right angles to the scattered beam of radiation.

* * * * *